United States Patent [19]

Bush et al.

[11] Patent Number: 5,382,516
[45] Date of Patent: Jan. 17, 1995

[54] METHOD AND DEVICES FOR DELIVERY OF SUBSTRATE FOR THE DETECTION OF ENZYME-LINKED, MEMBRANE-BASED BINDING ASSAYS

[75] Inventors: Christopher N. Bush, Richmond; Charlene A. Audette, Keene; Michael A. Harvey, Spofford, all of N.H.

[73] Assignee: Schleicher & Schuell, Inc., Keene, N.H.

[21] Appl. No.: 945,097

[22] Filed: Sep. 15, 1992

[51] Int. Cl.$^6$ .................. C12P 1/00; C12Q 1/34; C12Q 1/26; G01N 21/77
[52] U.S. Cl. .................. 435/41; 435/4; 435/7.1; 435/7.9; 435/14; 435/18; 435/19; 435/7.91; 435/21; 435/25; 435/28; 436/169; 436/170; 436/807
[58] Field of Search .......... 435/41, 14, 6, 4, 7.9, 435/18, 19, 21, 25, 28; 436/525, 810, 170, 169, 807

[56] References Cited

U.S. PATENT DOCUMENTS

| | | | |
|---|---|---|---|
| 4,452,901 | 6/1984 | Gordon et al. | 435/7.92 |
| 4,806,312 | 2/1989 | Greenquist | 422/56 |
| 4,808,529 | 2/1989 | Doppelfeld et al. | 435/14 |
| 4,818,677 | 4/1989 | Hay-Kaufman et al. | 436/810 |
| 4,826,759 | 5/1989 | Guire et al. | 436/170 |
| 4,857,652 | 8/1989 | Schaap | 549/510 |
| 4,870,005 | 9/1989 | Akiyoshi et al. | 436/170 |
| 4,950,588 | 8/1990 | Dattagupta | 435/6 |
| 4,952,707 | 8/1990 | Edwards et al. | 435/4 |
| 4,959,305 | 9/1990 | Woodrun | 435/7.92 |
| 4,966,856 | 10/1990 | Ito et al. | 436/170 |
| 4,975,366 | 12/1990 | Sudo et al. | 436/170 |
| 5,145,772 | 9/1992 | Voyta et al. | 435/4 |

OTHER PUBLICATIONS

Pollard-Knight, Denise et al., "Nonradioactive DNA Detection on Southern Blots by Enzymatically Triggered Chemiluminescence", Analytical Biochemistry, vol. 185, pp. 353–358 (1990).

Lumigen, Inc., "Chemiluminescent Detection With Luni-Phos TM 530", Detroit, Mich., (1990).

Primary Examiner—Michael G. Wityshyn
Assistant Examiner—Louise N. Leary
Attorney, Agent, or Firm—Cooper & Dunham

[57] ABSTRACT

The invention provides a method for supplying an enzyme substrate to a membrane-based, enzyme-linked reaction, comprising providing an open pore, high liquid retention capacity material impregnated with a predetermined amount of a substrate for the enzyme; and contacting the material with a membrane containing the enzyme-linked reaction under conditions which permit diffusion of the enzyme substrate to sites on the membrane containing the enzyme linked reaction. The invention further provides devices for membrane-based enzyme-linked reactions comprising a porous material impregnated with a predetermined amount of a substrate for the enzyme, wherein the porous material is paper, glass fiber paper, stainless steel mesh, woven and nonwoven nylon, polyester, polyethylene, polypropylene, or fluorocarbon polymers having a porosity ranging from about 5 microns to 5000 microns; and a microporous membrane of cellulose or a cellulose derivative, nylon, polysulfone, polypropylene, PTFE, or PVDF having a porosity ranging from about 0.05 microns to about 12 microns.

30 Claims, 3 Drawing Sheets

---

ENZYME LINKED MEMBRANE BINDING ASSAY

SUBSTRATE IMPREGNATED POROUS MATERIAL

FIG. 1

| ENZYME LINKED MEMBRANE BINDING ASSAY |
| SUBSTRATE IMPREGNATED POROUS MATERIAL |

FIG. 2

| SUBSTRATE IMPREGNATED POROUS MATERIAL |
| ENZYME LINKED MEMBRANE BINDING ASSAY |

METHOD AND DEVICES FOR DELIVERY OF SUBSTRATE FOR THE DETECTION OF ENZYME-LINKED, MEMBRANE-BASED BINDING ASSAYS

FIELD OF THE INVENTION

This invention relates to the enzyme-linked detection of binding reactions on porous substrates. In particular, this invention relates to an improved method of applying an enzyme substrate to an enzyme-linked membrane based reaction.

BACKGROUND OF THE INVENTION

The enzyme linked detection of binding reactions on porous substrates is well known in the art. For example, U.S. Pat. No. 4,452,901 (Gordon) discusses a method for transferring electrophoretically separated protein molecules from a gel to a porous nitrocellulose sheet, while preserving an exact replica of the electrophoretic separation. The separated, immobilized proteins can then be specifically probed, or further studied using antibodies. In order to localize the reaction on the membrane, however, the enzyme product must remain in the vicinity of the reaction. In many cases, this may be accomplished by the formation of an insoluble product which falls to the surface of the membrane around the reaction site. More recently, enzyme substrates yielding unstable products which further decay by emitting light have been tested (Pollard-Knight et al., *Analytical Biochemistry* 185, 353-358, 1990; U.S. Pat. No. 4,857,652). Since the unstable products are short-lived, they do not have time to diffuse far from the site of the reaction before light is emitted. The light signal may be captured on film.

In any enzyme reaction the rate of product formation is dependent on several factors. One of the most important is the concentration of the substrate available to the enzyme. For product formation to proceed at maximum rate, the concentration of the substrate must exceed the Km of the enzyme. If an enzyme reaction occurs in solution, the substrate which gets consumed by the reaction is rapidly replaced by new substrate contained in the solution. Where the enzyme is in an environment having a barrier to diffusion, however, the local concentration of substrate may decline as the reaction proceeds. This may eventually cause a decline in the rate of product formation. Maintaining high substrate concentration is therefore important to maximize the rate of product formation.

Normally, with membrane based enzyme linked reactions, the membrane is submersed in a solution of enzyme substrate which acts as a constant reservoir of substrate. In general this prevents the concentration of substrate from becoming too low or rate limiting, and allows the enzyme reaction to proceed as rapidly as possible. This method requires excess substrate, and the reaction continues for a long period of time. During that time, the measurement of product formation remains difficult. Some patentees have attempted to separate substrate from other reactants by constructing multi-zone devices where enzyme substrates are immobilized in a layer into which the reactants diffuse (see e.g., U.S. Pat. Nos. 4,806,312, 4,959,305 4,975,366). However, such devices contain the enzyme product within a particular location, and the enzyme substrate is not freely diffusible to the reaction site.

In the example of chemiluminescent substrates, such as the derivatives of the 1,2-dioxetanes, which can be used to detect a membrane-based reaction by exposing on film, an adamantyl derivative confers sufficient stability to the dioxetane to allow its use. Lumigen PPD (Lumigen, Inc. Detroit, Mich.), a form of dioxetane which can be dephosphorylated by alkaline phosphatase, generates an unstable phenolate anion AMP-D which eventually emits light. AMP-D, even though it has a half-life on the order of minutes, does not diffuse far from the site of enzymatic activity. In addition, the quantum yield of light from the dioxetane derivative is dramatically enhanced in this type of environment. The lack of diffusion is important because it allows the preservation of the resolution originally gained by the gel. Thus these dioxetane derivatives have been shown to be useful for detection of Western blots by accumulating the light signal on film.

In normal application, a membrane containing an enzyme-linked binding assay is submersed in a solution of substrate (dioxetane) and appropriate buffers and salts. Excess reagent is then drained from the blot, the membrane wrapped in plastic and exposed to X-ray film for varying periods of time. Following exposure of the blot to the dioxetane substrate there is a gradual increase in light production from those regions of the blot which contain enzyme. The rate of light production increases over a period of hours. When the maximum rate of light production has been reached the detection system is most sensitive. Thus, improvements in speed or sensitivity as well as improvements which use less substrate would be advantageous.

SUMMARY OF THE INVENTION

It is therefore a principal object of the invention to provide a method of applying an enzyme substrate to an enzyme-linked membrane-based reaction such that the enzyme reaction progresses more rapidly, is sustained longer, and is simpler to use. This and other objects are achieved, and the disadvantages of the prior art are overcome, by providing a method for supplying an enzyme substrate to a membrane-based, enzyme-linked reaction, comprising providing an open pore, high liquid retention capacity material impregnated with a predetermined amount of a substrate for the enzyme; and contacting the material with a membrane containing the enzyme-linked reaction under conditions which permit diffusion of the enzyme substrate to sites on the membrane containing the enzyme linked reaction.

Preferably, the membrane and porous material form a sandwich, the enzyme reaction emits light, and the light emitted from the sandwich is measured by a photodetector or exposes a film, such as x-ray film. Alternatively, the method may be carried out with an enzyme substrate combination which forms an insoluble, colored precipitate. The membrane may overlie the porous material or be placed beneath the material.

The porous material is preferably woven and nonwoven nylon, polyester, polyethylene, polypropylene, fluorocarbon polymers, or paper, glass fiber paper, or stainless steel mesh and should preferably have open pores from 5 to 5000 microns.

The membrane should preferably be a microporous membrane such as cellulose or a cellulose derivative, nylon, polysulfone, polypropylene, polytetraflouroethylene (PTFE) or polyvinylidene diflouride (PVDF) having a porosity ranging from about 0.05 microns to about 12 microns. The presently preferred membrane is a nylon microporous membrane, having a porosity ranging from 0.05 microns to about 1.0 micron.

Various enzyme substrate combinations may be used in practicing the method of the present invention. Preferably among those enzyme-substrate combinations are $\beta$-galactosidase and 3-galactosidoxyphenyl dioxetane, horseradish peroxidase and 4-chloro-1-napthol or luminol. Also, the enzyme may be alkaline phosphatase and the substrate is 5-bromo-4-chloro-3-indoxyl phosphate or 4-methoxy-4-(3-phosphatephenyl) spiro [1, 2-dioxetane-3, 2, 1-adamantine].

The invention further provides a method for supplying an enzyme substrate to a membrane-based, enzyme-linked reaction, comprising an open pore, high liquid capacity material selected from the group consisting of paper, glass fiber paper, or stainless steel mesh, woven and nonwoven nylon, polyester, polyethylene, polypropylene, and fluorocarbon polymers; impregnating the open pore material with a predetermined amount of a substrate for the enzyme; and contacting the open pore material with a microporous membrane containing the enzyme-linked reaction under conditions which permit diffusion of the substrate to sites on the microporous membrane containing the enzyme-linked reaction. Preferably, the enzyme is alkaline phosphatase and the substrate is 5-bromo-4-chloro-3-indoxyl phosphate or 4-methoxy-4-(3-phosphatephenyl) spiro [1, 2-dioxetane-3, 2, 1-iadamantine], and the porous material is nonwoven polyester, positioned beneath the microporous membrane.

The invention further provides a kit for membrane-based enzyme linked reactions comprising a porous material impregnated with a predetermined amount of a substrate for the enzyme. The porous material selected from the group consisting of paper, glass fiber paper, or stainless steel mesh woven and nonwoven nylon, polyester, polyethylene, polypropylene, and fluorocarbon polymers. The kit also includes a microporous membrane selected from the group consisting of cellulose derivative, nylon, polysulfone, polypropylene, polytetraflouroethylene (PTFE), or polyvinylidene difluoride (PVDF), preferably having a porosity ranging from about 0.05 microns to about 12 microns.

BRIEF DESCRIPTION OF THE DRAWINGS

Further features and advantages of the present invention may be understood by reference to the following detailed description taken together with the accompanying drawings in which:

FIG. 1 is a side view of a two layered test device having a substrate impregnated porous material beneath an enzyme linked membrane binding assay;

FIG. 2 is a side view of a two layered test device having a substrate impregnated porous material overlying an enzyme linked membrane binding assay;

DETAILED DESCRIPTION OF THE PREFERRED EMBODIMENTS

Figure 3:
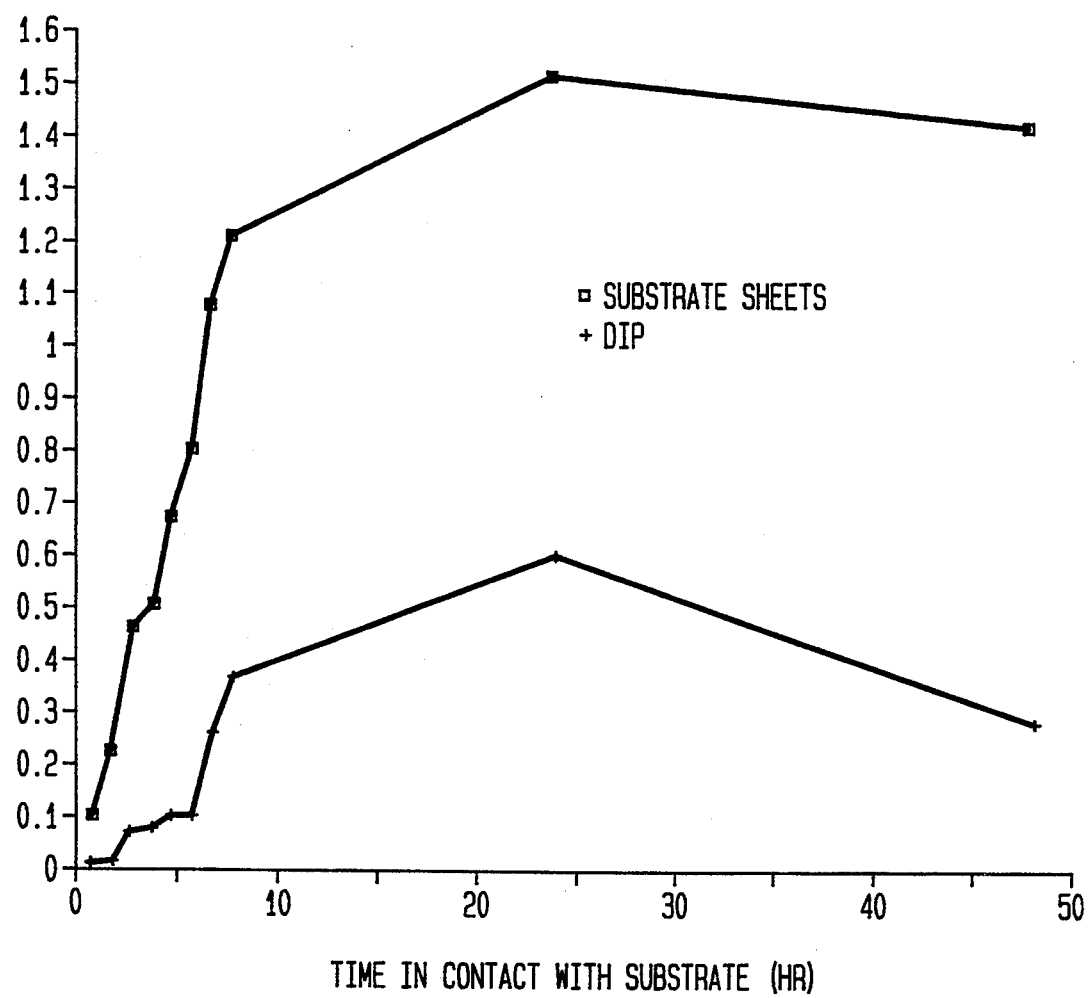
FIG. 3 is a graph comparing the chemiluminescence emitted from membranes using conventional methods of substrate application with methods of substrate application carried out in accordance with the methods of the present invention.

The present invention provides for a two layer sandwich, the first layer of which contains a specific amount of enzyme substrate in a freely diffusible form sandwiched with a porous membrane on which a binding reaction has been detected using an enzyme linked probe, as shown in FIGS. 1 and 2. The binding reaction detected can be the result of any one of a variety of commonly employed techniques involving either the direct immobilization of biomolecules, the electrotransfer of biomolecules or the passive transfer of biomolecules to a porous membrane. The position of the substrate containing material can either be on top (FIG. 1) or beneath (FIG. 2) the membrane layer of the sandwich. Preferably, the substrate containing material is beneath the enzyme containing layer.

The material used in the first layer can be of any one of a variety of common materials possessing sufficient open porosity and high liquid retention capacity to be able to accommodate an appropriate amount of enzyme substrate. The material must not react with the enzyme substrate and of itself it should possess no enzymatic activity. Appropriate materials include, but are not limited to, sheets of material composed of woven and nonwoven nylons, woven and nonwoven polyesters, woven and nonwoven polyethylene, woven and nonwoven polypropylene, woven and nonwoven fluorocarbon polymers and stainless steel meshes. Also appropriate for this purpose would be papers and glass fiber papers. The porosity or mesh opening of this material can range from about 5 to about 5000 microns. In a preferred embodiment, the material of the first layer is a nonwoven polyester such as Hollytex 3234, available from Ahlstrom Filtration Inc., Mount Holly Springs, Pa.

The material of the second layer, to which is attached the enzyme probed reaction, can be one of many commonly employed microporous membranes known to those skilled in the art. These include but are not limited to membranes composed of cellulose and its derivatives, nylons, PVDF, polysulfones, PTFE and polypropylene. These membranes should preferably have a porosity of about 0.05 microns to 12 microns. The material of the second layer could also be other appropriate flat sheet materials such as paper, derivatized paper, glass fiber paper or derivatized glass fiber paper. In a preferred embodiment the material of the second layer is a nylon microporous membrane having a porosity of about 0.45 microns.

The enzyme-substrate system employed in the method of this invention could be any such system capable of generating a localizable product. These would include, but are not limited to, horseradish peroxidase using substrates such as 4-chloro-1-naphthol to give an insoluble product or luminol to give a luminescent product; $\beta$-galactosidase using 3-galactosidoxyphenyl dioxetane (commercially available as Lumigen GPD) to generate a luminescent signal; and alkaline phosphatase using substrates such as 5-bromo-4-chloro-3-indoxyl phosphate in combination with nitroblue tetrazolium to yield an insoluble product or 4-methoxy-4-(3-phosphatephenyl)spiro[1,2-dioxetane-3,2,'-adamantane] available commercially as Lumigen PPD to yield a luminescent signal. In the preferred embodiment the enzyme-substrate system is alkaline phosphatase employing Lumigen PPD to yield a luminescent product. Other suitable enzyme-substrate systems are available, and are known to those skilled in the art.

The following examples are illustrative of the practices of the invention and are given to facilitate understanding and are not intended to be limiting.

EXAMPLE I

To determine the efficacy of the present invention, an immunoassay was performed on two nylon membranes. Three nanograms of a monoclonal anti beta-galactosidase antibody in 200 μL of Tris bufferred saline was applied to two 0.45 micron nylon membranes using a Minifold I apparatus (Schleicher and Schuell, Keene N.H.). Unoccupied sites on the membrane were then blocked with a 1% casein solution and the membrane subjected to a solution containing 20 ng/ml of an alkaline phosphatase conjugated goat anti-mouse Ig. Following washing, one of the membranes was dipped through 2 ml of Lumiphos 530 and the excess substrate solution allowed to drain off. The other was placed on the surface of a nonwoven polyester material (Hollytex 3234, Ahlstrom Filtration Inc, Mount Holly Springs, Pa.) containing 0.7 ml of Lumiphos 530. At various times following substrate application, the membranes were exposed to Kodak X-OMAT x-ray film for 10 minutes. The membranes were then removed from the film and the film developed. The developed film was then cut to size and the absorbance of the dots at 630 nm was measured in a Bio-Tek EL309 Microplate reader.

FIG. 3 shows that the dots from the membrane placed on top of the nonwoven material containing the luminescent substrate have significantly greater absorbance than those obtained from the membrane dipped in the same substrate. Each data point represents the mean absorbance of eight (8) replicate dots corrected for the background absorbance of the film. This results from increased light production from these areas of the membrane. The light production from the membrane on the substrate pad increases in intensity more rapidly and is sustained longer at a higher level than the membrane prepared using a traditional method (dipping) of substrate application.

EXAMPLE II

Figure 4:
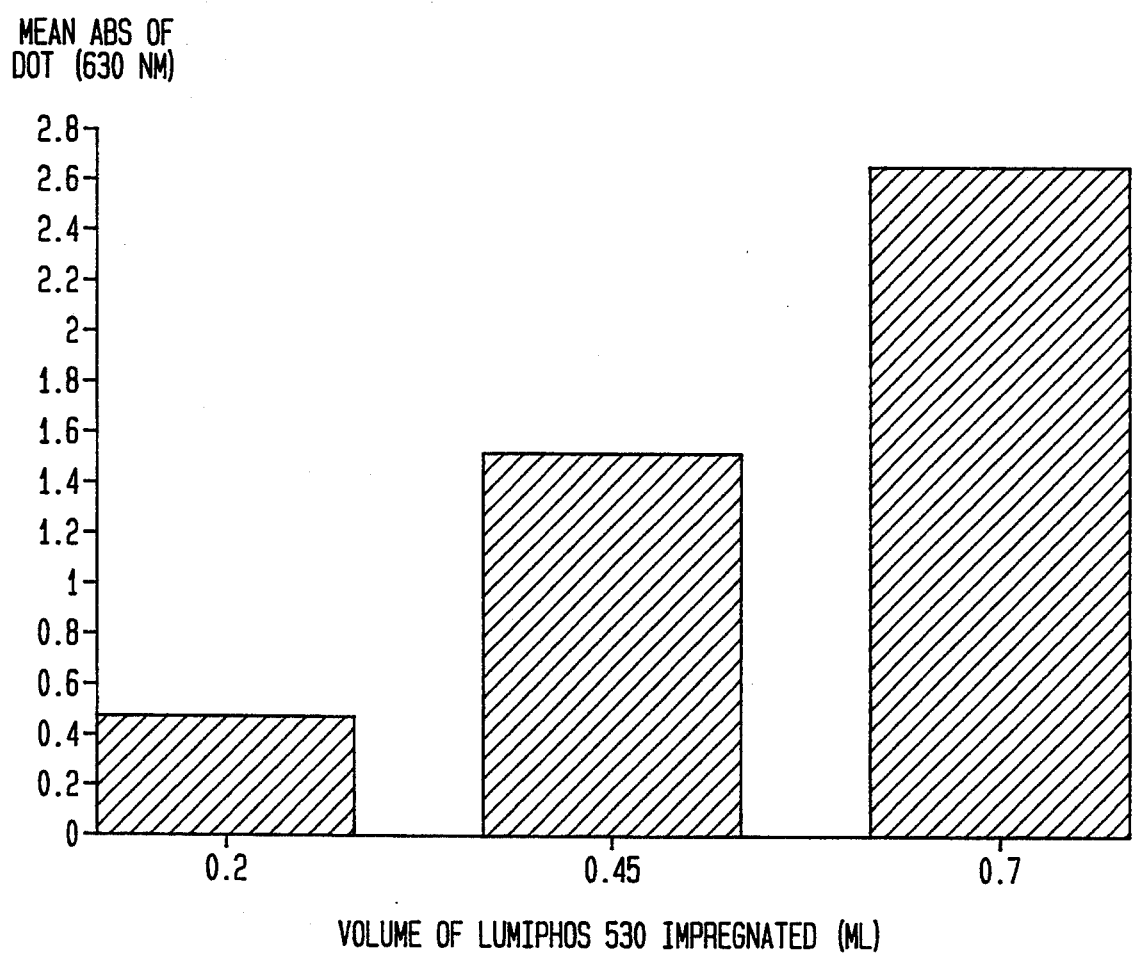
FIG. 4 is a graph comparing the effects of increasing amounts of substrate on product formation in accordance with methods of the present invention.

To determine whether the method of the present invention is dependent on the amount of substrate in the nonwoven material, different amounts of Lumiphos 530 were applied to individual sheets of the nonwoven material and separate nylon membranes bearing the immunoreaction described in Example I overlaid on top. The sandwiches were then exposed to X-ray film and the absorbance of the resulting dots measured. FIG. 4 shows that the intensity of light production is dependent on the amount of substrate impregnated in the nonwoven material. A membrane dipped in the substrate would contain about 180 μl of substrate and would have light production less than the sheet with the lowest amount of substrate impregnated with a predetermined or preselected amount of substrate.

We claim:

1. A method for supplying an enzyme substrate to a membrane-based, enzyme-linked reaction, comprising:
   providing an open pore, high liquid retention capacity material impregnated with a predetermined amount of a substrate for an enzyme, the substrate being free to diffuse from the material; and
   contacting the material with a membrane containing the enzyme in an enzyme-linked reaction under conditions which permit diffusion of the enzyme substrate to sites on the membrane containing the enzyme.

2. A method in accordance with claim 1, wherein the membrane and open pore material form a sandwich.

3. A method in accordance with claim 2, wherein the enzyme reacts with the substrate to emit light and the light is measured by a photodetector.

4. A method in accordance with claim 3 wherein the substrate is a 1,2-dioxetane substrate which yields a luminescent product.

5. A method in accordance with claim 2, wherein the enzyme reacts with the substrate to emit light and the light exposes a photographic film.

6. A method in accordance with claim 5, wherein the film is an x-ray film.

7. A method in accordance with claim 2, wherein the enzyme reacts with the substrate to form an insoluble detectable product.

8. A method in accordance with claim 3, wherein the membrane overlies the open pore material.

9. A method in accordance with claim 3, wherein the open pore material is woven and non-woven nylon, polyester, polyethylene, polypropylene, or fluorocarbon polymers.

10. A method in accordance with claim 5 wherein the open pore material is paper or stainless steel mesh.

11. A method in accordance with claim 9, wherein the open pore material has open pores from 5 to 5000 microns.

12. A method in accordance with claim 10 wherein the open pore material has open pores from 5 to 5000 microns.

13. A method in accordance with claim 9, wherein the membrane is a microporous membrane.

14. A method in accordance with claim 10, wherein the membrane is a microporous membrane.

15. A method in accordance with claim 13, wherein the microporous membrane is cellulose or a cellulose derivative, nylon, polysulfone, polypropylene, polytetraflouroethylene, or polyvinylidene diflouride, and has a porosity ranging from about 0.05 microns to about 12 microns.

16. A method in accordance with claim 14, wherein the microporous membrane is cellulose or a cellulose derivative, nylon, polysulfone, polypropylene, polytetraflouroethylene, or polyvinylidene diflouride, and has a porosity ranging from about 0.05 microns to about 12 microns.

17. A method in accordance with claim 13, wherein the membrane is a nylon microporous membrane, and has a porosity ranging from 0.05 microns to about 1.0 micron.

18. A method in accordance with claim 14, wherein the membrane is a nylon microporous membrane having a porosity ranging from 0.05 microns to about 1.0 micron.

19. A method in accordance with claim 17, wherein the enzyme is β-galactosidase and the substrate is 3-galactosidoxyphenyl dioxetane.

20. A method in accordance with claim 18, wherein the enzyme is β-galactosidase and the substrate is 3-galactosidoxyphenyl dioxetane.

21. A method in accordance with claim 17, wherein the enzyme is horseradish peroxidase and the substrate is 4-chloro-1-napthol or luminol.

22. A method in accordance with claim 18, wherein the enzyme is horseradish peroxidase and the substrate is 4-chloro-1-napthol or luminol.

23. A method in accordance with claim 17, wherein the enzyme is alkaline phosphatase and the substrate is 5-bromo-4-chloro-3-indoxyl phosphate or 4-methoxy-4-

(3-phosphatephenyl) spiro [1, 2-dioxetane-3, 2, 1-adamantine].

24. A method in accordance with claim 10, wherein the paper is glass fiber paper.

25. A method for supplying an enzyme substrate to a membrane-based, enzyme-linked reaction, comprising:
providing an open pore, high liquid capacity material selected from the group consisting of paper, stainless steel mesh, woven and nonwoven nylon, polyester, polyethylene, polypropylene, and fluorocarbon polymers;
impregnating the open pore material with a predetermined amount of a substrate for the enzyme; and
contacting the open pore material with a microporous membrane containing the enzyme-linked reaction under conditions which permit diffusion of the substrate to sites on the microporous membrane containing the enzyme-linked reaction.

26. A method in accordance with claim 25, wherein the paper is glass fiber paper.

27. A method in accordance with claim 25, wherein the enzyme is alkaline phosphatase and the substrate is 5-bromo-4-chloro-3-indoxyl phosphate or 4-methoxy-4-(3-phosphatephenyl) spiro [1, 2-dioxetane-3, 2, 1-adamantine], and wherein the open pore material is nonwoven polyester, positioned beneath the microporous membrane.

28. A method in accordance with claim 27, wherein the microporous membrane is nylon having a porosity of between about 0.3 to about 0.6 microns.

29. A kit for membrane based enzyme linked reactions comprising:
a porous material impregnated with a predetermined amount of a substrate for an enzyme, the porous material selected from the group consisting of paper, stainless steel mesh, woven and nonwoven nylon, polyester, polyethylene, polypropylene, and fluorocarbon polymers having a porosity ranging from about 5 microns to about 5000 microns; and
a microporous membrane selected from the group consisting of cellulose derivative, nylon, polysulfone, polypropylene, polytetraflouroethylene, or polyvinylidene diflouride having a porosity ranging from about 0.05 microns to about 12 microns.

30. A method in accordance with claim 29, wherein the paper is glass fiber paper.

* * * * *